US008739670B2

(12) United States Patent
Coulombe

(10) Patent No.: US 8,739,670 B2
(45) Date of Patent: Jun. 3, 2014

(54) METHOD AND APPARATUS FOR TRIMMING MATERIAL FROM A WEB

(75) Inventor: Benoit Coulombe, Drummondville (CA)

(73) Assignee: SCA Hygiene Products AB, Göteborg (SE)

( * ) Notice: Subject to any disclaimer, the term of this patent is extended or adjusted under 35 U.S.C. 154(b) by 0 days.

(21) Appl. No.: 14/001,008

(22) PCT Filed: Mar. 15, 2011

(86) PCT No.: PCT/EP2011/053916

§ 371 (c)(1),
(2), (4) Date: Aug. 22, 2013

(87) PCT Pub. No.: WO2012/123024

PCT Pub. Date: Sep. 20, 2012

(65) Prior Publication Data

US 2013/0331250 A1 Dec. 12, 2013

(51) Int. Cl.
*B26D 7/14* (2006.01)
(52) U.S. Cl.
USPC .................................. 83/872; 83/18
(58) Field of Classification Search
USPC ............... 83/13, 18, 870–874, 373, 375, 175, 83/176, 151, 154, 155
See application file for complete search history.

(56) References Cited

U.S. PATENT DOCUMENTS 5,199,446 A * 4/1993 Cahill et al. .................. 131/84.1

(Continued)

FOREIGN PATENT DOCUMENTS

| GB | 2 322 822 A | 9/1998 |
| WO | WO 97/00654 A1 | 1/1997 |
| WO | WO 2010/126415 A1 | 11/2010 |

OTHER PUBLICATIONS

International Search Report (PCT/ISA/210) issued on Nov. 17, 2011, by the European Patent Office as the International Searching Authority for International Application No. PCT/EP2011/053916.
Written Opinion (PCT/ISA/237) issued on Nov. 17, 2011, by the European Patent Office as the International Searching Authority for International Application No. PCT/EP2011/053916.

(Continued)

*Primary Examiner* — Sean Michalski
(74) *Attorney, Agent, or Firm* — Buchanan Ingersoll & Rooney PC

(57) ABSTRACT

Unattached elastic portions of an elasticised web are grasped and raised above a support surface for feeding the elasticised web. The raised portions are brought into contact with a knife blade that is positioned to protrude through the thickness of the raised elastic layer into free space so as to remain spaced from the support surface that is moving beneath the blade in a direction normal to the support surface. The raised elastic layer is held raised during trimming with the knife blade by an elevation element over which the elastic layer runs. A grasping device holds the unattached portion being cut in a taut state in the cross machine direction. The elastic layer thus spans across the elevation element and the grasping device. The knife blade extends through the thickness of the elastic layer along the spanned part of the elastic layer into free space.

25 Claims, 9 Drawing Sheets

(56) References Cited

U.S. PATENT DOCUMENTS

| | | | |
|---|---|---|---|
| 5,325,874 A * | 7/1994 | Heitmann | 131/84.4 |
| 5,376,203 A * | 12/1994 | Syme | 156/209 |
| 5,695,846 A * | 12/1997 | Lange et al. | 428/98 |
| 6,176,164 B1 * | 1/2001 | Nylander | 83/21 |
| 6,702,917 B1 * | 3/2004 | Venturino et al. | 156/252 |
| 6,913,718 B2 * | 7/2005 | Ducker et al. | 264/37.1 |
| 2006/0032589 A1 * | 2/2006 | Nakakado et al. | 156/494 |
| 2007/0031634 A1 * | 2/2007 | Allison et al. | 428/95 |
| 2011/0154964 A1 * | 6/2011 | Sato | 83/19 |
| 2013/0101805 A1 * | 4/2013 | Altshuler et al. | 428/172 |

OTHER PUBLICATIONS

International Preliminary Report on Patentability (PCT/IPEA/409) issued on Feb. 8, 2013, by the European Patent Office as the International Searching Authority for International Application No. PCT/EP2011/053916.

* cited by examiner

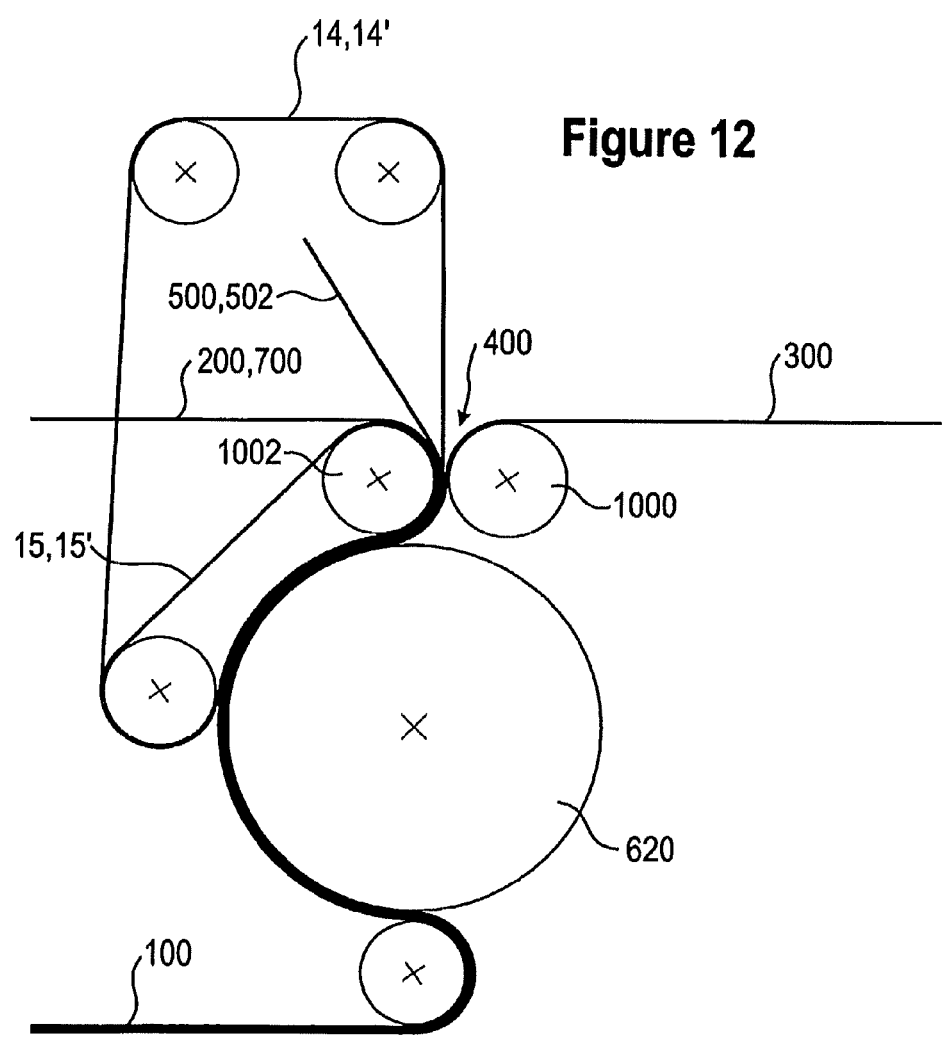

METHOD AND APPARATUS FOR TRIMMING MATERIAL FROM A WEB

FIELD OF THE INVENTION

The present disclosure is concerned with a method and an apparatus for trimming material from a web. In particular, the present disclosure is concerned with trimming an elastic layer attached to a first web from the first web. Yet more particularly, the present disclosure is concerned with trimming elastic threads from a first web, where the elastic threads are arranged along the first web in an undulating configuration so that when the trimmed portions are removed, the elastic strands are arranged in discrete portions separated in the machine direction. The resulting webs are to be used in the manufacture of an absorbent article, such an incontinence pants, baby diapers and infant diapers. The elastic layer or elastic threads may ultimately form leg elastics in the absorbent article.

BACKGROUND TO THE DISCLOSURE

WO 2010/126415 discloses a method and apparatus for manufacturing an elasticised web having discrete elastic thread portions separated in a machine or longitudinal direction of the elasticised web. The resulting elasticised web is disclosed to be formed into a front waist region or a rear waist region of an absorbent article and the elastic threads provide front or rear waist region leg elastics. The separation between the elastic thread portions in the machine direction forms a crotch portion in the absorbent article that is free of elastic threads in the lateral direction of the absorbent article, which is often desirable.

FIGS. 1 to 5 of the present application are reproductions of selected figures from WO 2010/126415 and will be discussed in detail in the following as an aid to the reader in understanding the background to the present disclosure and to give an understanding of the preferred application of the present disclosure.

Referring to FIG. 1, there is disclosed a second web 200 and a first web 300 being fed in the machine direction MD. Also fed in the machine direction is at least one elastic thread, preferably a group of 2, 3 or more elastic threads, 500 that is arranged on the second web 200 as a wave extending in the machine direction forming an undulating pattern that goes back and forth in the cross machine direction CD. The group of elastic threads 500 are attached to the first web using a spray of adhesive 250. The undulating pattern and the arrangement of the group of elastic threads 500 is such that portions of the group of elastic threads 500 protrude out from a cross machine direction CD edge 203 of the second web 200 and a cross direction CD edge 303 of the first web 300. Accordingly, the group of elastic threads 500 are arranged as portions overlapping and attached to the second web 200 separated in the machine direction MD by portions protruding from the edge 203 of the first web 200 and the edge 303 of the second web 300. The attached portions of the elastic threads will form first and second leg elastics of an absorbent article when the elasticised web 300 is manufactured into an absorbent article. The unattached portions of the elastic threads 500 are to be trimmed away from the second web 200 so that the attached portions become discrete portions of elastic threads separated and unconnected from one another in the machine direction. The separation between adjacent attached portions of the elastic threads 500 in the machine direction MD provide a location for attachment of an absorbent core 3 from the elastic threads 500.

The unattached portions of the elastic threads 500 are trimmed away using a rotary knife 605 that can be better viewed in FIG. 2. Further details of the elastic trimming means of the prior art are detailed below.

Continuing to refer to FIG. 1, a first web 300 is fed so as to be positioned over the second web 200 and laminated thereto so as to sandwich the attached portions of the elastic threads 500, yet leave the unattached portions protruding from the laminate of the first and second webs 200, 300 for trimming using the rotary cutter 605. The laminate of the first and second webs 200, 300 and the discrete elastic thread portions provide an elasticised web 100 that can subsequently be formed into a front waist region or a rear waist region of an absorbent article.

In order to manufacture an absorbent article from the elasticised web 100, a second such elasticised web 100 can be placed parallel to the first elasticised web 100 yet spaced therefrom in the cross machine direction as shown in FIG. 3. A further web 900 can bridge the cross machine directional space between the first and second elasticised webs 100 to connect them to one another. Similarly, an absorbent core 130 can overlap the first and second webs 100 in the cross machine direction and bridge the space between the first and second elasticised webs 100. A cross machine direction cut C can be made to separate the web absorbent article 100, 900, 130 into discrete absorbent articles and leg holes can be made by stamping out the shaded region S to provide leg contours having leg elastics following the leg contours except at the region overlaid by the absorbent core 130.

Referring to FIG. 2 of the present application, the apparatus and method for trimming the protruding portions of elastic threads can be understood more fully. As can be seen, the second web 200, the first web 300 and the elastic threads 500 are sandwiched together at a nip 400 between rollers. At this stage, the laminate has unattached portions of the elastic threads protruding from a side edge thereof that have yet to be trimmed away. The protruding, unattached portions of the elastic threads 500 are gripped between first and second belts 401, 402, which is perhaps more clearly illustrated in FIG. 1. The unattached, protruding portions of the elastic threads 500 are thus held in position in the cross machine direction and in the machine direction MD so that they are held taut and are manageable during the trimming process. The laminate of the first and second webs 300, 200 and the elastic threads 500 is held against the outer surface of a rotating drum 620 in order to provide a support surface for the laminate and to feed the laminate passed the rotary cutter 605. As can be seen from FIG. 2, the first and second belts 401, 402 are arranged to move correspondingly with the movement of the outer surface of the drum 620 so that the protruding portions of the elastic threads 500 are kept in fixed relation relative to the laminate 200, 300, 500.

With the laminate 200, 300, 500 held against the outer surface of the drum 620 and with the protruding portions of the elastic threads 500 gripped between the first and second belts 401, 402, the rotary cutter 605 is pressed against the outer surface of the drum 620 so as to cut through the protruding portions of the elastic threads 500 at the edge of the laminate 200, 300, 500 in order to trim the unattached portions of the elastic threads 500 to thereby provide the laminate 100 with discrete portions of elastic threads separated in the machine direction.

At least two problems have been found with the press cutting arrangement of the prior art. A first problem is that the engagement between the blade of the rotary cutter 605 and the outer surface of the drum 620 tends to wear at the sharpness of the blade, requiring relatively frequent maintenance to sharpen the blade or relatively frequent replacement of the blade. The other problem is that the deforming nature of the elastic threads 500 tends to result in the elastic threads 500 occasionally not being cut, even if the drum 620 is provided with an elastic backing surface for reception of the blade of the cutter 605. Accordingly, one objective of the present disclosure is to provide a means and method of trimming material away from a web, particularly elastic material and, even more particularly, elastic threads, that is able to reduce a maintenance burden and is also able to ensure a better rate of cutting success of the material.

An alternative method and apparatus for manufacturing an elasticised web for use in manufacturing an absorbent article as disclosed in WO 2010/126415 will be described with reference to FIGS. 4 and 5 of the present application.

In the method and apparatus of FIGS. 4 and 5, a single elasticised web is formed that can be manufactured into an absorbent article by the addition of an absorbent core 130 and a suitable cross directional cutting step and a stamping out step without requiring first and second elasticised webs to be separately formed and connected by a bridging web 900 as in the method and apparatus of FIGS. 1 to 3.

More specifically, second and third webs 200, 700 are fed in side-by-side relation to a nip 400 at which nip the second and third webs 200, 700 are laminated to a first web 300. Sandwiched between the second web 200 and the first web 300 is at least one first elastic thread or a first group of elastic threads 500 attached to the second web 200 and arranged in an undulating pattern 500 as shown above with respect to FIG. 1. Similarly, at least one second elastic thread or a second group of elastic threads 502 is sandwiched between the third web 700 and the first web 300 in a path extending along the machine direction and undulating in the cross machine direction CD. The second and third webs 200, 700 are laminated to the first web 300 in an arrangement separated from one another in the cross machine direction so that the first web 300 is exposed in a central area in the cross machine direction CD. Like in the method and apparatus discussed above with respect to FIGS. 1 to 3, the first and second elastic threads 500, 502 are partially attached to the first web 300 at portions sandwiched respectively between the second and the third webs 200, 700 and the first web 300.

There are also unattached portions of the first elastic threads 500 protruding from the laminate of the second web 200 and the first web 300 and there are also unattached portions of the elastic threads 502 that protrude from the laminate of the third web 700 and the first web 300. These unattached, protruding portions of the elastic threads 500, 502 are to be trimmed away in order to provide the resulting elasticised web 100 with discrete portions of elastic threads 500, 502 that are separated from one another in the machine direction. There is thus provided a row of first discrete portions of the elastic threads 500 extending in the machine direction of the resulting elasticised web 100 and a second row of discrete portions of the second elastic threads 502, where the first and second rows are separated from one another in the cross machine direction and arranged such that the discrete portions of elastic threads 500, 502 are aligned with one another in the machine direction as can be seen in FIG. 5. The unattached portions protrude toward one another in a central region of the first web 300 in the cross machine direction CD where the cross machine directional separation of the second and third webs 200, 700 is located.

In order to trim the protruding, unattached portions of the elastic threads 500, 502, a trimming operation is to be carried out. As with the apparatus and method disclosed with respect to FIGS. 1 to 3, the protruding unattached portions of the first elastic threads 500 are to be grasped between first and second belts 401, 402 and held taut as they are moved with the laminate of webs 200, 300, 700 passed a press cutter 605. The first and second belts 401, 402 are arranged respectively on an upper surface of the first web 300 and a lower surface of the first web 300 such that both the unattached portions of the first elastic threads 500 and the first web 300 are held between the first and second belts 401, 402. The laminate of webs 200, 300, 700 are held against the outer surface of a drum 620 to act as a support surface against which the blade of the press cutter 605 can press in order to cut through the protruding portions of the first elastic threads 500. A second such cutting mechanism 605' is provided adjacent to the first cutting mechanism 605 in the cross machine direction for cutting the protruding portions of the second elastic threads 502. Again, the laminate of webs 200, 300, 700 is held against the outer surface of the drum 620 and the protruding portions and the first web 300 are gripped between third and fourth belts 403, 404 as they are trimmed away by a second press cutter 605'. Like the first press cutter 605, the second press cutter 605' is arranged so that the blade thereof presses against the outer surface of the drum 620 so as to cut through the second elastic threads 502.

The resulting elasticised web 100 can be manufactured into discrete absorbent articles by attaching an absorbent core 130 between the discrete portions of elastic threads in the machine direction of the elasticised web 100, cutting the elasticised web in the cross machine direction at C and stamping out material to form leg contours at S. A first row of the discrete elastic portions forms leg elastics for one of a front waist region and a rear waist region of the resulting absorbent article and a second row of the discrete elastic portions forms leg elastics for the other of the front and rear waist regions of the resulting absorbent article. Adjacent discrete portions in the machine direction of the elasticised web 100 ultimately form leg elastics for the left and right legs respectively once the elasticised web is cut and further formed into discrete absorbent articles. The manufacturing method of FIGS. 4 and 5 is more efficient in some ways as compared to the manufacturing method of FIGS. 1 to 3 since the formation of separate first and second elasticised webs 100 that then have to be connected together by a bridge of material is not required. The method of cutting away the unattached, protruding portions of elastic threads 500, 502 is complicated. That is, the first and second press cutters 605, 605' cannot be pressed against the outer surface of the drum 620 continuously as can be done in the method and apparatus of FIGS. 1 to 3 because this would split the elasticised web 100 into three parts in the cross machine direction CD. Thus, the first and second press cutters 605, 605' are pressed intermittently against the outer surface of the drum 620 in synchronisation with the elasticised threads so as to cut the unattached, protruding portions of the elastic threads 500, 502 and to intermittently leave the laminate uncut in between the unattached, protruding portions of the elastic threads 500, 502 in the machine direction MD. While this does allow an efficient method and apparatus for manufacturing absorbent articles, the intermittent press cutters 605, 605' leaves slits in the first web 300 where the elastic threads 500, 502 have been cut. The slits are not always desirable.

Another object of the present disclosure is, therefore, to provide a method and apparatus for trimming material, that is attached to a web, away from the web in a manner that allows the web to be held against a support surface and extend underneath a knife edge for trimming away the material without the web itself also being cut.

SUMMARY

In view of the above objectives, the present disclosure provides a method of trimming material from a web in a method of manufacturing an absorbent article, the trimming method comprising:

feeding the web and holding it against a support surface;

holding material to be trimmed elevated from the support surface and elevated relative to the web as the web is fed against the support surface;

trimming the elevated material from the web with a blade that is spaced from the support surface.

A traditional approach to cutting a web fed, and held tight against, a support surface (such as a drum) would be to press a blade of a rotary knife against the support or drum surface. This can be problematic since the material being cut from the web may not be cut all the way through its thickness by the blade pressing against the support surface, or an anvil portion thereof. Very common elastic threads are Lycra® type. These threads are multifilament threads. When cutting such threads, it sometimes happens that one (or a few) filaments remain uncut. An unsuccessful cut can thus result. This problem with cutting is especially prevalent where the material being cut is an elastic layer because, it is believed, the elastic property tends to deform the layer about the blade or knife edge to increase the risk of the elastic layer not being completely cut. Further, the pressing of the blade against the support surface tends to wear the blade, which can result in undesirably frequent maintenance of the blade in terms of sharpening it or replacing it with a new one.

According to the method of the present disclosure, the material to be cut is held spaced above the support surface and the blade is placed in the feed path of the elevated material so that the material is cut as it passes the blade, while the knife edge is able to remain spaced from the support surface. As such, the material is successfully cut from the web and the blade remains free of contact with the support surface to avoid undue wear.

As should be clear from the above, it is a preferred feature of the disclosure for the material to be trimmed to be part of an elastic layer attached to the web.

Preferably, the blade protrudes beyond the elevated material in the thickness direction of the elevated material toward the support surface yet is spaced from the support surface, thereby ensuring that the knife edge penetrates the full thickness of the material to be trimmed. Thus, the knife edge or blade extends through the thickness of the material into free space. The spacing of the blade is in a direction normal to the support surface. That is, the support surface is positioned directly underneath the blade in the direction normal to the support surface.

In a preferred embodiment, the elevated material extends in the cross machine (with respect to the machine direction feeding of the web) direction with the cross machine extension of the support surface so that the elevated material is located above the support surface in a direction normal to the support surface.

Preferably, an elevation element is used to hold the material elevated above the support surface such that the blade severs the elevated material as it passes over the elevation element in the machine direction.

This feature provides a support block against which the elevated material can be pressed during trimming to ensure a successful cut.

Preferably, the blade is located adjacent the elevation element in the cross machine direction of the web.

Yet more preferably, the elevated material is held taut against the elevation element so that the blade severs the taut elevated material. Cutting taut material improves the chances of a successful cut.

Preferably, the web is fed in the machine direction by corresponding movement of the support surface in the machine direction.

The support surface preferably moves in the machine direction relative to the elevation element. Preferably, the elevation element is spaced from the support surface so that the first web is able to pass thereunder also in spaced relation from the elevation element. Preferably, the elevation element is sized so as to space the material from the support surface by a distance of between 1 mm and 10 mm.

In a further preferred embodiment, the material has a free end side in the cross machine direction and a side attached to the web. In a preferred embodiment, the material is grasped by a grasping means moving in conjunction with the support surface so that the web and the material to be cut move together. The grasping means may hold the elevated material taut as it is cut by the blade. The grasping means may be in the form of a clamp, clamping on a support surface side and an opposed side thereof while still moving in the machine direction with the web. Preferably, the material is so clamped as to be held taut against the elevation element.

In a preferred embodiment, the grasping means rests on the web or is marginally spaced therefrom as it grasps the material in an elevated position relative to the web. Put another way, the web is positioned between the grasping means, e.g. a first belt, and the support surface in a direction normal to the support surface. Preferably, the grasping means comprises first and second belts that grasp the material therebetween. Preferably, the web is positioned between the first belt and the support surface.

In a preferred embodiment, the elevated material spans first and second elevation elements for elevating the material from the support surface in a taut manner, whereby the knife edge is positioned between the elevation elements to trim the elevated material. Cutting of such bridged material has been found to ensure a successful cut.

Preferably, the first elevation element is the elevation element described above and the second elevation element is the grasping means, e.g. the first belt of the grasping means, described above.

In a preferred embodiment, an elevation element for elevating the material from the support surface is arranged so that the web is able to travel underneath it as the material travels above it, thereby elevating the material from the web so that it can be trimmed without cutting the underlying web. In a preferred embodiment, the method comprises feeding the web on the support surface underneath the elevation element, preferably in a manner so that the web moves relative to the elevation element in the machine direction, and elevating the material to be cut from the web with the elevation element, whereby the blade trims the elevated material from the web by extending through the thickness of the elevated material into free space, spaced from the web and the support surface. The terms "underneath" and "spaced" in the foregoing are to be understood in the context of a direction normal to the support surface. The web and the support surface are cross machine directionally coincident with the blade. That is, they extend in the cross-machine direction at least to a position underlying the blade.

According to this embodiment of the disclosure, it is possible to cut away the trim material while holding the web flat against the support surface without cutting or otherwise physically intervening with the travel of the web along the support surface.

Put another way, the blade edge protrudes through the thickness of the material toward the support surface as the material is held elevated from the web and the support surface, yet only protrudes so far as a position spaced from the web.

The arrangement of the elevation element so the web can pass underneath it on the support surface allows the trimming apparatus to cut material, e.g. elastic thread, even when the web extends underneath the elevation element and the knife blade in the cross-machine direction without the knife blade cutting the underlying web. This is advantageous as compared to the configuration disclosed above with respect to FIGS. 4 and 5, wherein the underlying web is intermittently slit. This spaced arrangement of the elevation element relative to the support surface can also be used with narrower webs in the cross machine direction that are not so wide as to pass underneath the elevation element.

In a preferred embodiment, the web travels underneath an elevation element (so that the web is between the elevation element and the support surface in a direction normal to the support surface) and a grasping means, whereby the grasping means holds the material in an elevated position relative to the support surface taut against the elevation element and the blade is positioned between the elevation element and the grasping means in the cross-machine direction so as to cut through the material yet remain spaced from the support surface and the underlying web, whereby the web grasping means and the support surface move correspondingly in the machine direction relative to the elevation element and the blade so that the elevated material is trimmed from the web as the material and the web move in the machine direction and the web thus comes into contact with the blade.

Preferably, the web remains held flat against the support surface as the material to be cut is raised therefrom.

The trimming method of the present disclosure is preferably used in the context of trimming an elastic layer, preferably elastic threads, from a web so that the web is provided with discrete elastic portions separated from one another in the machine direction to, ultimately, provide leg elastics of an absorbent article.

In an aspect of the disclosure, there is provided a method of manufacturing an elasticised web in a method of manufacturing an absorbent article, the elasticised web having discrete elastic portions separated from one another in a machine or longitudinal direction of the elasticised web, the method comprising:
   feeding a first web supported on a support surface in a machine direction;
   partly attaching an elastic layer to the first web so as to define an undulating path along the first web in the machine direction;
   grasping unattached portions of the elastic layer;
   holding the unattached portions in an elevated position from the support surface; and
   trimming the unattached portions of the elastic layer while they are grasped, elevated and moving in the machine direction with the first web using a blade or knife edge that protrudes through the thickness of the elevated portion of the layer toward the support surface yet spaced from the support surface to thereby cut the elastic layer into discrete portions separated from one another in the machine direction.

This ensures successful cutting of the unattached portions of the elastic layer since the knife edge protrudes through the elastic layer, yet ensures a low maintenance knife edge because it does not run pressed against the support surface. Further, even through the unattached portions are raised from the support surface, the web advantageously remains held flat against the support surface.

Preferably, a second web is laminated to the first web so as to sandwich the attached portions of the elastic layer between them and so that the unattached portions protrude in the cross machine direction relative to the first web, the second web or both from the laminate to be so grasped, elevated and trimmed according to the above method.

Such an elasticised laminate is preferably used to form a front waist region or a rear waist region or both of an absorbent article. The discrete elastic portions are preferably shaped and arranged to, ultimately, provide front or rear or both leg elastics. Thus, the elastic layer is preferably in the form of a plurality of elastic threads for forming leg elastics of the absorbent article.

All of the features described above with respect to the material trimming method are applicable to the present aspect of the disclosure.

An apparatus for trimming material from a web, the apparatus comprising:
   a moving support surface for feeding the web held thereagainst in a machine direction;
   an elevation element for elevating material attached to or part of the web from the support surface; and
   a knife blade positioned to protrude through the thickness of the elevated material as it is held in the elevated position by the elevation element and yet is spaced from the support surface to thereby trim material from the web.

Elevating the material for trimming enables an improved success rate of cutting, while spacing the blade from the support surface ensures longevity of the knife blade.

In a further preferred embodiment, the apparatus comprises a grasping means for holding the material to be cut in a fixed position relative to the moving web and for holding the material taut against the elevation element in the elevated position, whereby the knife blade is positioned between the grasping means and the elevation element to cut through the taut, elevated material. The grasping means could be a vacuum grasper or other known means but is preferably moving belts forming a nip therebetween in which the material is held. Preferably, the grasping means forms a second elevation element for elevating the material to be trimmed from the support surface so that the material spans across the first and second elevation elements during trimming thereof with the knife blade. The grasping means may alternatively form the elevation element, thereby performing both the material grasping and material elevating functions.

The apparatus preferably further comprises an elastic layer applicator that partly attaches an elastic layer to the first web such that the elastic layer extends in the machine direction and undulates in the cross machine direction to follow an undulating path and such that a cross machine directional part of the undulating path is attached to the web and a cross machine directional part of the undulating path is unattached to the web, whereby the elevation element is positioned to elevate the unattached part of the elastic layer and the knife blade is positioned to trim the elevated, unattached part of the elastic layer from the web, thereby forming discrete elastic portions separated form one another in the machine direction of the web.

In a preferred embodiment, the apparatus comprises a second web feeding mechanism arranged to bring said web, which is a first web, and said second web together and a laminator to form a laminate sandwich of the elastic layer and the first and second webs, whereby the unattached part of the elastic layer protrudes in the cross machine direction from the laminate.

In a further preferred embodiment, the apparatus comprises a converter taking the laminate of the first and second webs having the attached part of the elastic layer sandwiched therebetween and the unattached part trimmed away by the knife blade and converting it into at least a front waist region or a rear waist region of an absorbent article such that the space in the machine direction between the discrete elastic portions is made into an absorbent core, crotch region of at least the front or rear waist region and the elastic portions on either side thereof form leg elastics for respective leg openings of at least the front or rear waist region of the absorbent article.

In a preferred embodiment, the support surface is formed by the outer surface of a rotating drum.

In a further preferred embodiment, the elevation element is arranged relative to the support surface so that the web is positioned underneath the elevation element and remains held against the support surface as the material to be trimmed away is positioned over the elevation element so as to be held in an elevated position relative to the web and the support surface for cutting through its thickness with the knife blade that is positioned to protrude through the thickness of the elevated material yet remain spaced from the web and the support surface. In a preferred embodiment, the support surface is arranged to move in the machine direction relative to the elevation element.

Such a cutting mechanism allows the material to be cut away without cutting through an underlying web, which can remain held flat against the support surface during trimming. Thus, the cutting mechanism can be used to successfully trim the elastic threads in a method and apparatus as disclosed above with reference to FIGS. 1 to 3 and also in a method and apparatus as disclosed above with reference to FIGS. 4 and 5 since the first web can pass underneath the elevation element as the first and second rows of unattached parts of the elastic threads are elevated and cut away. The cutting mechanism of the present disclosure is not required to move into intermittent engagement with the elastic threads, nor does it make intermittent slits in the first web, as with the method and apparatus of FIGS. 4 and 6.

BRIEF DESCRIPTION OF THE FIGURES

FIG. 12 is a schematic view of the cutting apparatus based on the apparatus of FIG. 4 showing a necessary modification to the path of the first and third grasping belts in order to implement the cutting means of the present disclosure whereby the elastic is raised from the underlying web.

DETAILED DESCRIPTION OF THE PREFERRED EMBODIMENTS

Figure 1:
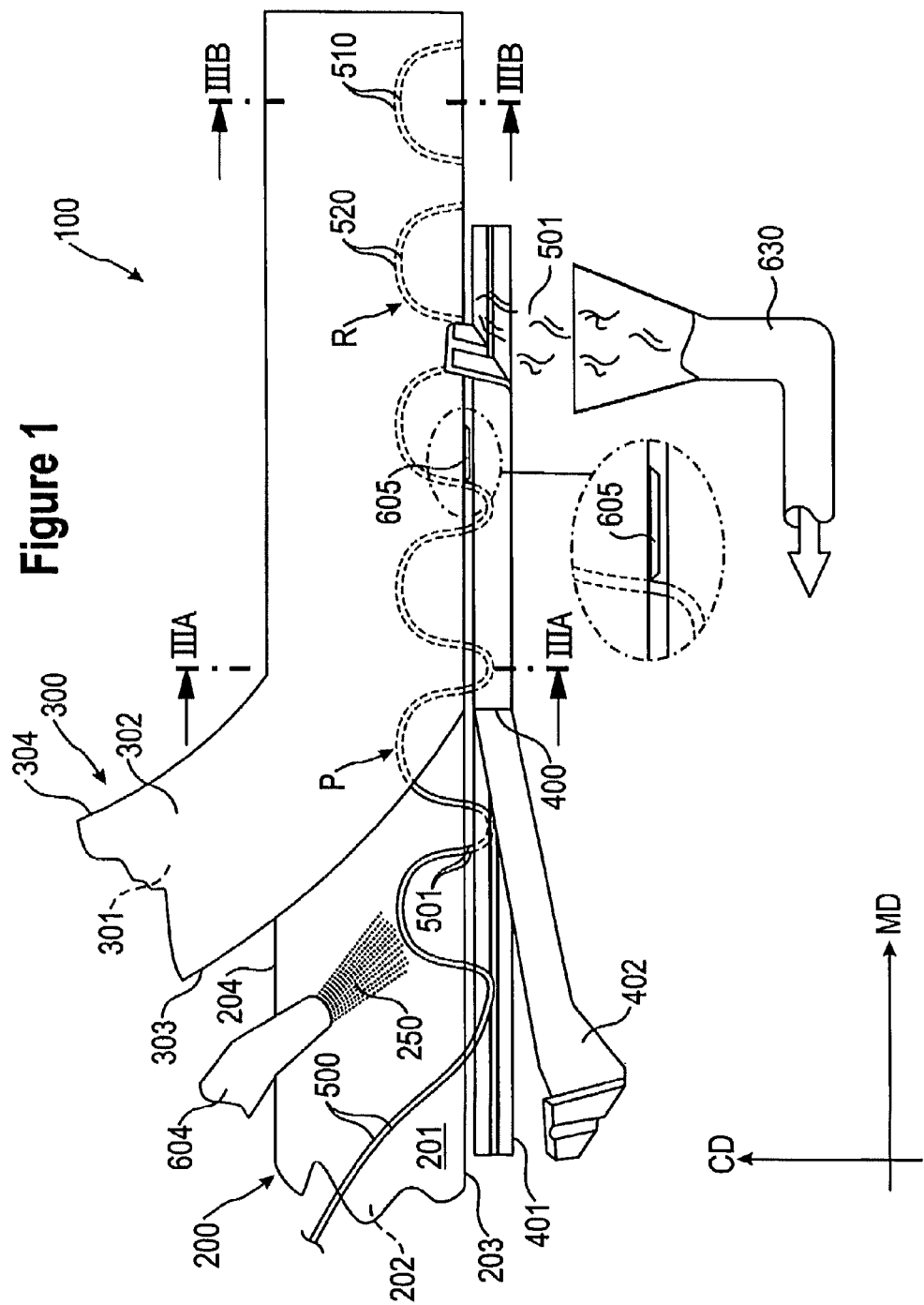
FIGS. 1 to 3 disclose a prior art method and apparatus for forming an elasticised web, whereby a continuous wave of elastic threads extending in the machine direction is trimmed at portions protruding from a laminate of a first web and a second web so as to provide an elasticised web having discrete portions of elastic threads separated in the machine direction for forming leg elastics of an absorbent article.

The present disclosure is concerned with improving a trimming means and method for trimming material from a web that is held against a support surface. The trimming means and method of the present disclosure is particularly useful for application in a means and method for manufacturing an elasticised web as disclosed above with respect to FIGS. 1 to 3 and FIGS. 4 and 5 and as disclosed in WO 2010/126415. Thus, the following detailed description of exemplary trimming means and methods with reference to the figures will be given in the context of replacing the press cutter 605, 605' of the prior art with a new trimming means that is able to trim the elastic threads away from a web with a greater cutting success rate, with a blade that requires less maintenance and without cutting the underlying web.

More specifically, the present disclosure provides a means and method whereby a web is held on a moving support surface, preferably provided in the form of an outer surface of a rotating drum. The web has attached thereto a continuous elastic layer in the machine direction of movement of the web. The elastic layer, preferably at least one elastic thread, is formed in a wavy or undulating pattern extending in the machine direction. Each repeating unit of the pattern can be seen as comprising a crest part and a trough part. The crest part is attached to the web, preferably using adhesive. The trough part is unattached to the web and is to be trimmed away so that the elastic layer pattern is to be broken into discrete portions separated from one another in the machine direction, where the space between the discrete portions are ultimately to form a crotch region of an absorbent article and the contoured elastic portions formed on either side of the space are to form at least part of leg elastics of an absorbent article. This aspect of the preferred embodiment of the present disclosure is familiar to the prior art document WO 2010/126415.

It is the manner by which the unattached portions are trimmed away that the present disclosure concerns itself with. According to an embodiment of the present disclosure, the unattached elastic portions are grasped and raised above the support surface. The raised portions are brought into contact with a knife blade that is positioned to protrude through the thickness of the raised elastic layer into free space so as to remain spaced from the support surface that is moving beneath the blade in a direction normal to the support surface. In a preferred form, the raised elastic layer is held raised during trimming with the knife blade by an elevation element over which the elastic layer runs. Grasping means holds the unattached portion being cut in a taut state in the cross machine direction. The elastic layer thus spans across the elevation element and the grasping means. The knife blade extends through the thickness of the elastic layer along the spanned part of the elastic layer into free space.

In a preferred form, the web is positioned under the elevation element and the grasping means as the elastic layer is held aloft from the support surface and the web by the elevation element and the grasping means for trimming by the knife blade. In an elasticised web making method and apparatus as in FIGS. 4 and 5 discussed above whereby the web is required to pass underneath the trimming blade, the underlying web is not slit by the blade since the elastic layer is elevated from the web and the support surface and the blade protrudes through the thickness of the elastic layer but not so far as to engage the underlying web and support surface.

The knife blade may be a rotary blade that is preferably actively rotated (i.e. it is not passively rotated by rolling against the support surface as in the prior art; it is self powered and thus capable of operating at a speed different from the speed of the support surface) in a reverse direction to the direction of movement of the web and the elastic layer.

Figure 5:
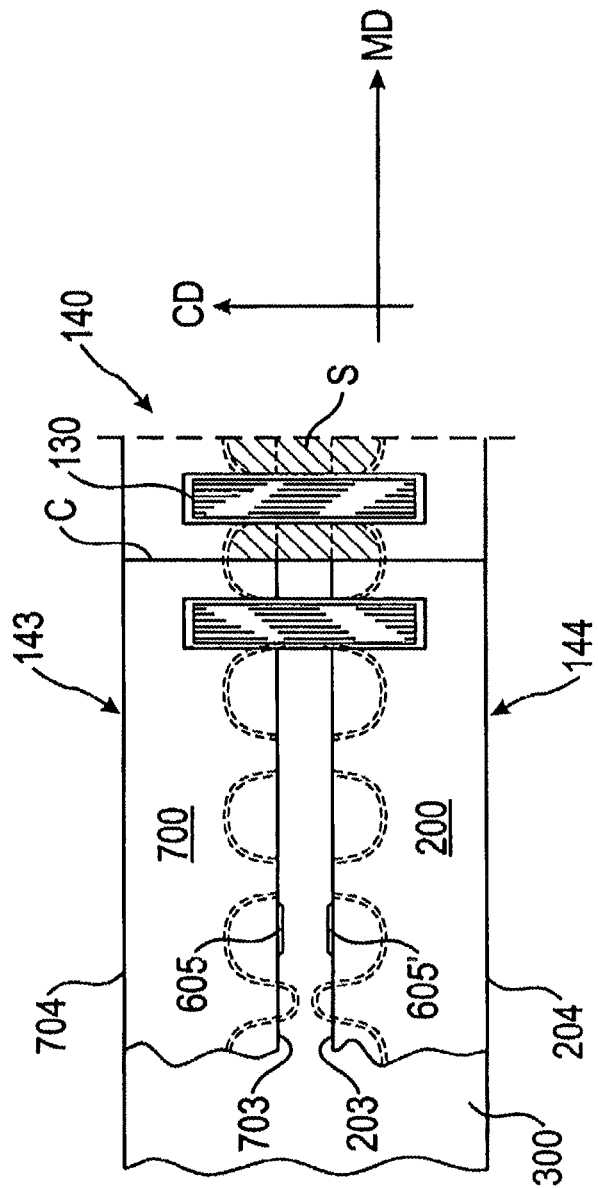
Figure 6:
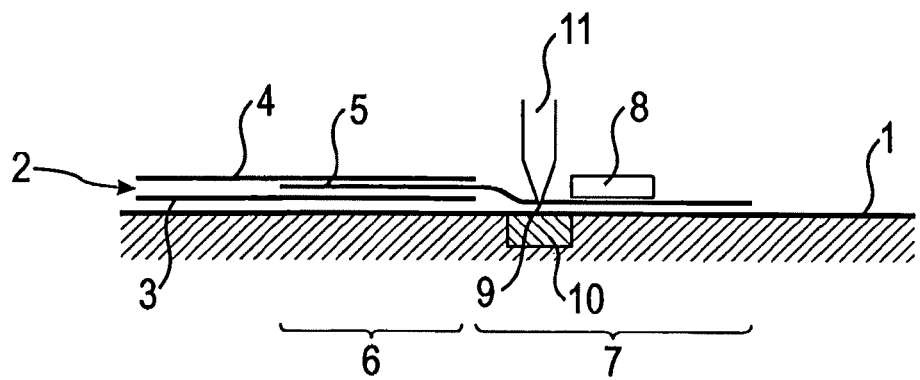
FIG. 6 discloses a press cutter of the prior art, whereby elastic threads are cut by pressing a knife blade into a backing support surface through the elastic threads. The laminate is held against the support surface, which feeds the elastic threads protruding from the laminate to the press cutter.

FIG. 6 shows a support surface 1 having held thereon a laminate 2. The support surface 1 may be an outer surface of a rotating drum such as the rotating drum 620 shown in FIGS. 1 to 5. The laminate 2 is a laminate of a first web 3, a second web 4 and elastic threads 5 sandwiched between the first and second webs 3,4. The laminate 2 could thus have been made according to the process shown in FIGS. 1 to 3, where there is a laminate of a first web 300, a second web 200, and elastic threads 500 sandwiched between them. As with the laminate of FIGS. 1 to 3, the elastic threads 5 of FIG. 6 have a cross machine directional part 6 attached to at least the first web 3 and, in the shown embodiment, the first and second webs 3,4. The elastic threads also have a cross machine directional part 7 that is unattached to the first and second webs 3, 4 and protrudes in the cross machine direction from the first and second webs 3,4.

A grasping means 8 is provided to grasp the unattached, protruding portion of the elastic threads 5 to the support surface 1 so as to hold the elastic threads 5 on the support surface 1 during and after, for a short time, trimming of the unattached portion 7 of the elastic threads 5. The support surface 1 and the grasping means 8 move together at the same speed so as to move the laminate 2 and the elastic threads 5 passed the trimming blade 9 in the machine direction so that the trimming blade 9 severs the elastic threads 5 at a position adjacent in the cross machine direction to the edge of the first and second webs 3,4 of the laminate 2 from which the elastic threads 5 protrude.

The cutting mechanism of FIG. 6 is a press cutter comprising a rotary cutter 11 having a blade 9 for cutting the elastic threads 5. The support surface 1 comprises a backing portion 10 of relatively resilient material against which the blade 9 of the rotary cutter 11 presses in order to cut through the unattached portion 7 of the elastic threads 5. A similar type of press cutter is disclosed to be used in the prior art method and apparatus of FIGS. 1 to 5. As has been explained above, it occurs more frequently than is desirable for some of the elastic threads 5 to remain uncut, especially when cutting one ore more multifilament threads. Further, the forceful interaction of the blade 9 and the backing portion 10 of the support surface 1 tends to wear the blade. It is from such a prior art cutting apparatus that the present disclosure has been conceived.

It has been recognised that cutting the elastic threads by running them into a blade that penetrates beyond the threads and which rests in free space overcomes the above described difficulties with wear and uncut threads. Thus, with reference to FIG. 7 a modification of the cutting means of FIG. 6 is shown. Only those features different from FIG. 6 will be described in detail. The description given above with reference to FIG. 6 is applicable to FIG. 7 for all same components.

Figure 7:
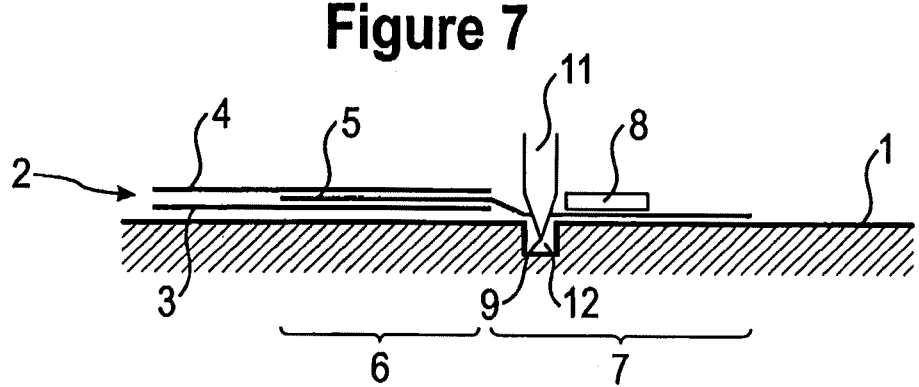
FIG. 7 discloses an improvement of the cutting mechanism of FIG. 6 in terms of cutting rate success since the cutting blade protrudes through the thickness of the elastic threads into free space by protruding into a groove in the support surface.

The trimming apparatus of FIG. 7 differs from that in FIG. 6 in that the support surface 1 is provided with a groove 12 that the blade 9 penetrates into. The unattached portion 7 of the elastic threads 5 are thus held against the support surface 1 by the grasping means 8 and the blade penetrates beyond the protruding threads 5 into the groove 12 to a significant degree (e.g. about 5 mm into the groove relative to the support surface 1) to thereby increase a successful cut rate. The groove 12 would be a circumferential grove in the case of the support surface 1 being provided by an outer periphery of a rotating drum. The blade 9 is sitting in free space in the groove and thus does not engage with the support surface 1. Accordingly, the rate of wear of the blade 9 is much reduced. The cutter 11 is preferably a rotary cutter that operates in reverse rotation to the direction of movement of the support surface 1. The rotary cutter is actively rotated in the reverse direction. An exemplary speed for the rotation of the blade is 2000 rpm. Other blade configurations could be used such as a static blade that sits in the groove 12 and is stationary. The cutting is performed by the elastic threads 5 moving with the support surface 1 and the grasping means 8 relative to the blade 9. An exemplary cutting mechanism of this kind, although in a different technical field to the manufacture of absorbent articles and even of cutting elastic threads, is known from GB 2322822, for example.

Figure 2:
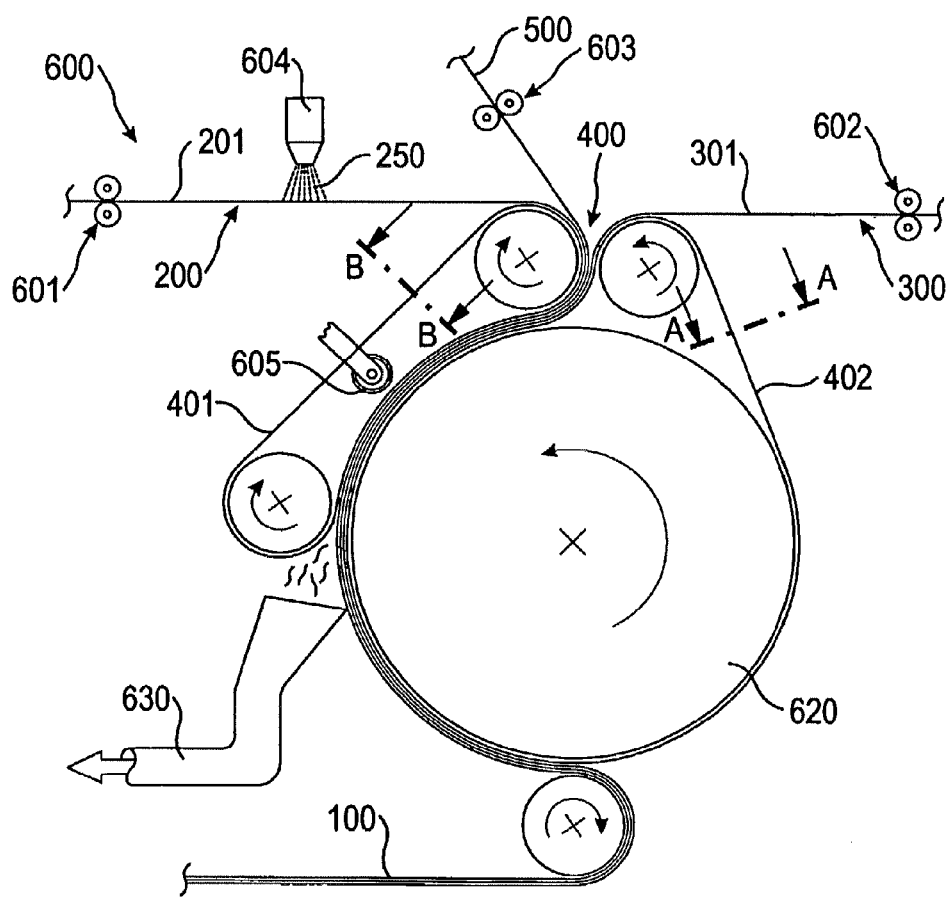
Figure 3:
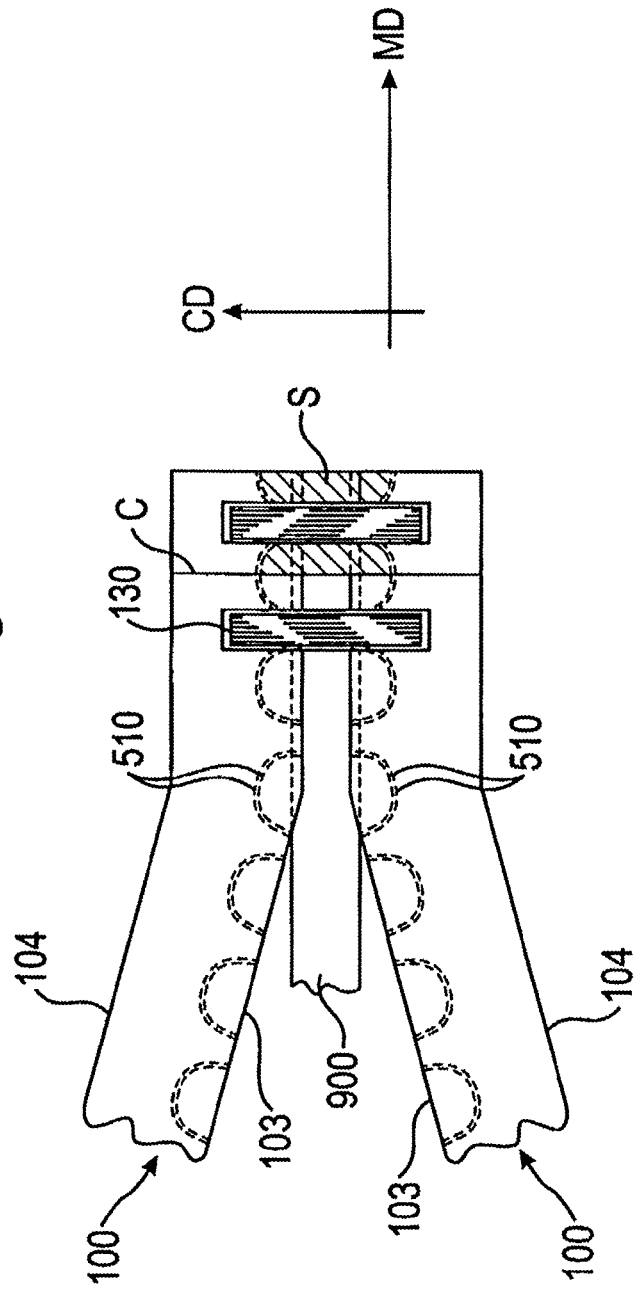

It would be appreciated by the skilled person that the cutting mechanism of FIG. 7 is, in the preferred application, intended to be incorporated into the means and method of FIGS. 1 to 3 in place of the cutting blade 605 so as to trim the protruding portions held between the belts 401, 402 of the elastic threads 500 protruding from the edge of the laminate of the first and second webs 300, 200. That is, the drum 620 is to be provided with a groove 12 within which the blade 9 of the rotary cutter 11 is to penetrate to trim the elastic threads 500 as they are moved passed the blade 9 and over the groove 12.

Figure 8:
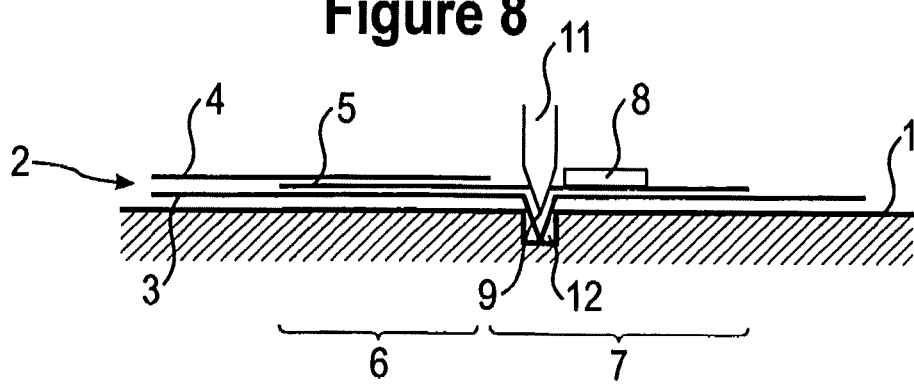
FIG. 8 discloses the cutting mechanism of FIG. 7 as applied to a laminate whereby the elastic strands and a first web of the laminate extends to a position underneath the blade. The first web extends into the groove as the elastic threads are cut, which disfigures the first web.

While the solution for trimming elastic threads of FIG. 7 is an improvement of the press cutter of FIG. 6 in terms of elastic cut success rate, it does have disadvantages as will be discussed with reference to FIG. 8. The discussion of FIG. 7 above is applicable to the apparatus of FIG. 8. The difference from FIG. 7 in the apparatus of FIG. 8 is that it is being used with a laminate having a first web 3 that extends in the cross machine direction beyond the blade 9 and groove 12. As a result of the extended first web 3, the first web 3 is forced into the groove 12 by the blade providing a disfigured portion of the first web 3 that does not rest flat against an even support surface 1. This disfigurement of the first web 3 is often unacceptable in absorbent article manufacturing and in other applications.

Figure 4:
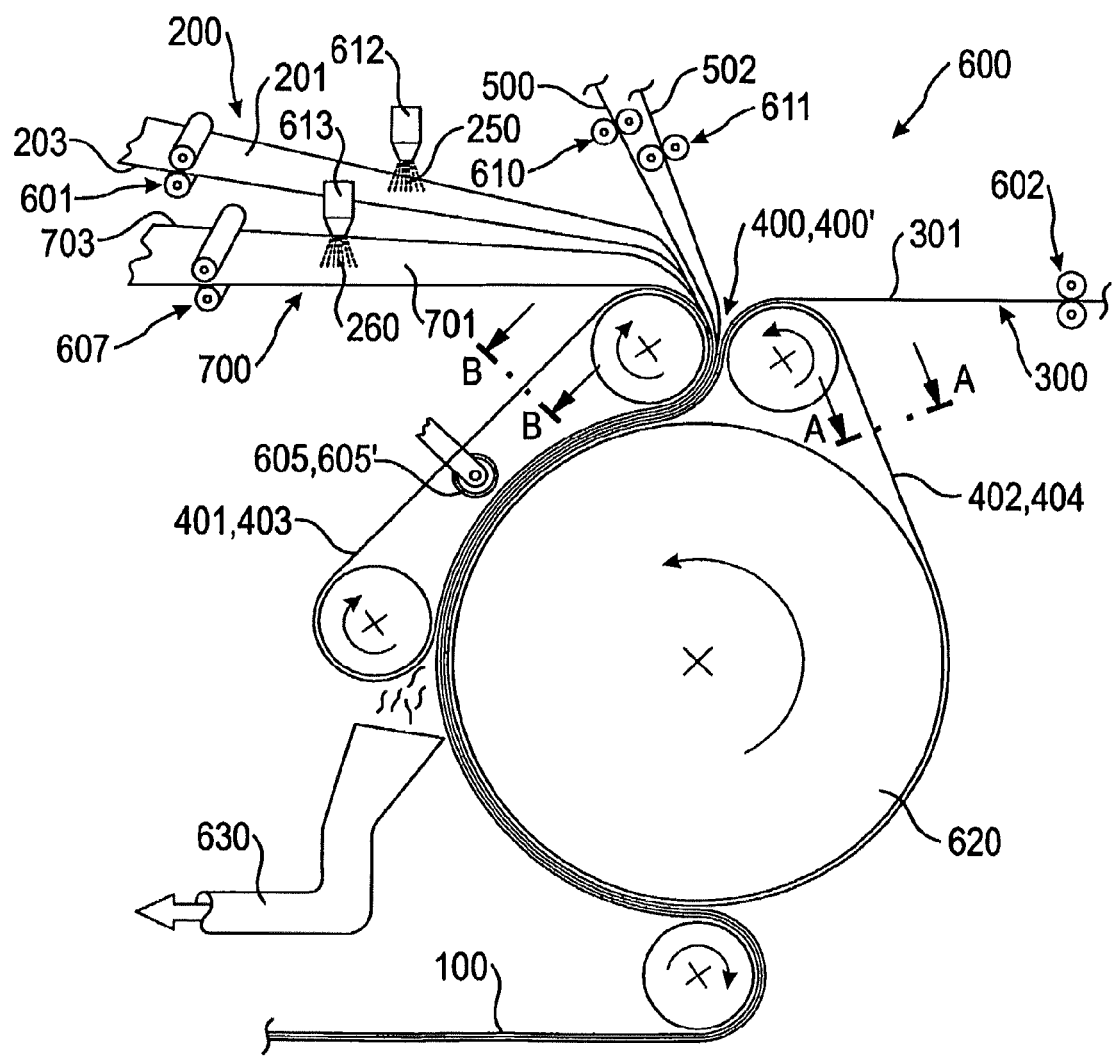
FIGS. 4 and 5 disclose a prior art method and apparatus for forming an elasticised web that differs from the web of FIGS. 1 to 3 by forming first and second waves of elastic threads extending in the machine direction and spaced from one another in the cross machine direction. Laminates are formed on either side of the elasticised web within which the first and second waves of elastic threads are respectively sandwiched. The first and second elastic threads protrude out from the laminates in a central region of the elasticised web to be trimmed away so as to form the elasticised web with first and second rows of discrete portions of elastic threads separated from one another in the machine direction. The rows of discrete portions of elastic threads are for respectively forming front and rear leg elastics of an absorbent article.

It would be clear to the skilled person that the cutting mechanism of FIG. 8 is, in the preferred application, to be used in place of the cutting mechanism for trimming the first and second protruding elastic thread portions 500, 502 of FIGS. 4 and 5. That is, the first press cutter 605 is to be replaced with a first blade 9 and groove 12 arrangement as shown in FIG. 8 and the second press cutter 605' is to be replaced with a second blade 9 and groove 12 arrangement as shown in FIG. 8. The web 3 is akin to the first web 300 and the support surface 1 is akin to the outer peripheral surface of the drum 620. The drum 620 of FIG. 4 would thus be provided with first and second parallel grooves 12 having blades 9 protruding therein adjacent one another in the cross machine direction in the same arrangement as the blades 605, 605' shown in FIG. 5. The first and second blades would be for respectively trimming away elastic threads 500, 502 protruding in the cross machine direction from the second and third webs 200, 700. As discussed above, a disadvantage of this arrangement is that the first web would be disfigured with two parallel indentations running in the machine direction where the first and second blades 9 force the first web 300 into the first and second grooves 12 at respective cross machine directional locations.

Figure 9:
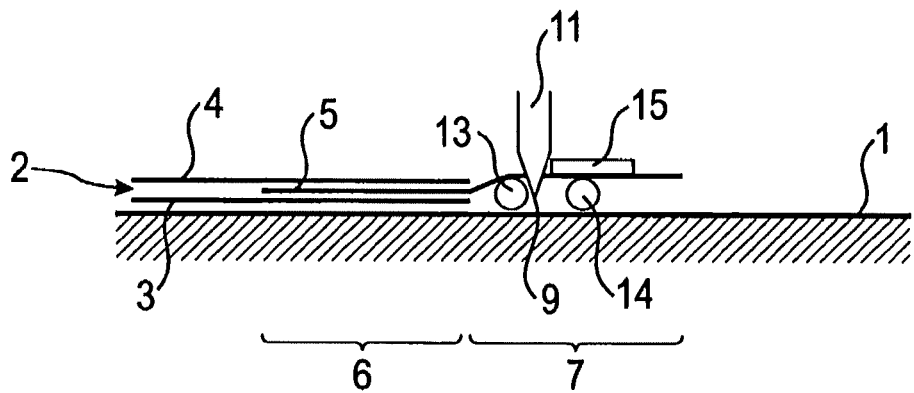
FIG. 9 discloses a trimming mechanism according to an embodiment of the present invention. The elastic threads are elevated from the laminate support surface and span first and second elevation elements, whereby a blade protrudes through the thickness of the elastic threads at the span portion without coming into engagement with the underlying support surface.

FIG. 9 shows an embodiment of a cutting means and method according to the present disclosure. As in the means of FIGS. 6 and 7, a laminate 2 of first and second webs 3, 4 sandwiching elastic threads 5 is fed on a support surface. The elastic threads are attached between the first and second webs 3,4 and protrude at discrete locations along the machine direction from an edge of the first and second webs 3, 4 and are to be trimmed away in order to form discrete elasticized portions in the laminate 2 along the machine direction.

In order to trim a protruding, unattached portion 7 of the laminate 2, it is grasped at a free end most distal from the edge of the first and second webs between first and second belts 14,15. The first and second belts 14,15 move in conjunction with the machine directional movement of the support surface 1 (and thus the laminate 2) and serve to hold the protruding portion 7 of the elastic threads 5 a fixed distance from the edge of the first and second webs 3,4 during trimming with the blade 9. Further, an elevation element 13 is provided to raise the protruding portion 7 of the elastic threads 5 from the support surface at a location directly adjacent the cross machine directional edge of the first and second webs 3,4. The first and second belts 14,15 also serve to provide a second elevation element 14 spaced from the first elevation element 13 in the cross machine direction more distal from the edge of the first and second webs 3,4 than the first elevation element 13.

In the cross machine directional space between the first elevation element 13 and the second elevation element 14, a blade 9 protrudes toward the support surface 1 beyond a straight elevation line extending between the top surfaces of the first and second elevation elements 13, 14 so that elastic threads 5 elevated from the support surface 1 and moving in the machine direction passing the blade 9 are trimmed away.

In a preferred embodiment, the elevation element is raised from the support surface by a distance of 5 mm to 10 mm and the bottom of the blade floats above the support surface by at least 2 mm and below the top of the elevation element or elements by at least 2 mm. As discussed above, the blade is preferably a rotary cutter, preferably rotating in a reverse direction to the direction of movement of the elastic threads at a speed of at least 2000 rpm, but may be a static one.

Referring to FIGS. 1 to 3, the cutting mechanism of FIG. 9 is preferably applied so as to trim the elastic threads 500 protruding from the laminate of the first and second webs 200, 300. That is, the threads 500 are grasped between the belts 14,15 similar to belts 401, 402 but raised from the support surface 1 provided by the rotating drum 620 as shown in FIG. 1. An elevation element 13 is installed so as to raise the protruding elastic threads 500 from the support surface 1 at a position adjacent the edge 203,303 of the first and second elastic webs 200, 300. A rotary cutter 11 is installed in place of the cutter 605 in a cross machine directional space between the elevation element 13 and the belts 14,15 and protrudes toward the support surface beyond the elevated elastic threads 500 to trim them away from the laminate of the first and second webs 200,300. The blade 9 protrudes into free space floating above the support surface 1. Such a cutting arrangement ensures successful cutting of the elastic threads 500.

Figure 10:
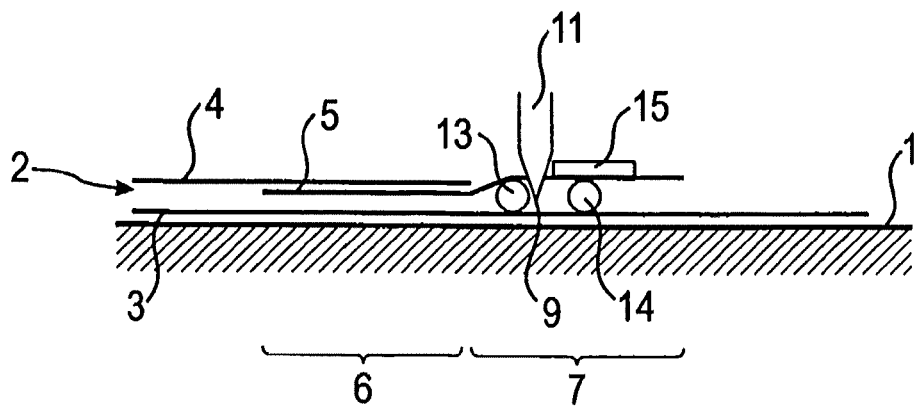
FIG. 10 discloses the same trimming mechanism as FIG. 9 as applied to a laminate, whereby a first web of the laminate extends so as to rest on the support surface underneath the first and second elevation elements, whereby the blade protrudes through the elevated elastic threads spanning the first and second elevation elements without coming into engagement with the first web and the support surface.

The cutting apparatus of FIG. 10 is the same as that in FIG. 9, but is used in a different way. More specifically, the first web 3 is positioned underneath the elevation element and the first and second belts 14, 15 so that the elastic threads 5 protrude from a cross machine directional edge of the second web 4. Thus, the elevation element 13 positioned adjacent the edge of the second web 4 raises the protruding portion 7 of the elastic threads 5 from the first web 3 held flat against the support surface 1 as does the second elevation element 14 formed by the first belt 14 of the grasping means 14, 15. In this way, the elevation element 13 and the elevation element 14 are positioned between the first web 3 and the unattached portion 7 of the elastic threads 5 in a direction normal to the support surface 1. The trimming means of FIGS. 9 and 10 allows the advantage of improved cutting success rate of the trimming means of FIG. 6 by having the blade 9 protrude through the thickness of the material to be cut with the blade floating in free space. Another advantage is allowing the first web 3 to be supported evenly against a flat support surface 1.

The cutting means and method of FIG. 10 is preferably applied in place of the trimming mechanism of FIGS. 4 and 5. In order to do so, it is required to install first and second such cutting means to replace the cutting rollers 605, 605' of FIGS. 4 and 5. Thus, with reference to FIG. 11, there is shown first and second knife blades 11, 11' arranged to trim away first and second elastic threading 5, 5' grasped respectively between first and second grasping belts 14, 15 and third and fourth grasping belts 14', 15'. A first web 3 is supported on the support surface 1. Second and third webs 4, 4' are laminated respectively at opposed sides of the first web 3 in the cross machine direction to be spaced apart in a central region of the first web 300. First and second elastic layers 5, 5', e.g. first and second multifilament elastic threads, protrude respectively from the edges of the second and third webs 4, 4' into the central region. It is in the central region that the first and second elastic threadings are grasped respectively by the first and second grasping means 14, 15, 14', 15', elevated respectively by the first elevation elements 13, 13' and second elevation elements 14, 14' (formed by a first belt 14, 14' of the grasping means 14, 15, 14', 15') and cut respectively by the knife blades 11, 11' respectively protruding through the thickness of the first and second elastic threads 5, 5' at a portion bridging the elevation elements 13, 14, 13', 14'. Noteworthy is that the grasping belts 14, 15, 14', 15' and the first elevation elements 13, 13' are arranged with respect to the support surface so that the first web 3 passes underneath them. This feature enables the elastic threads 5, 5' to be raised not only from the support surface 1 but also to be raised from the first web 3 without interfering with the first web 3 laying flat on the support surface 3.

Figure 11:
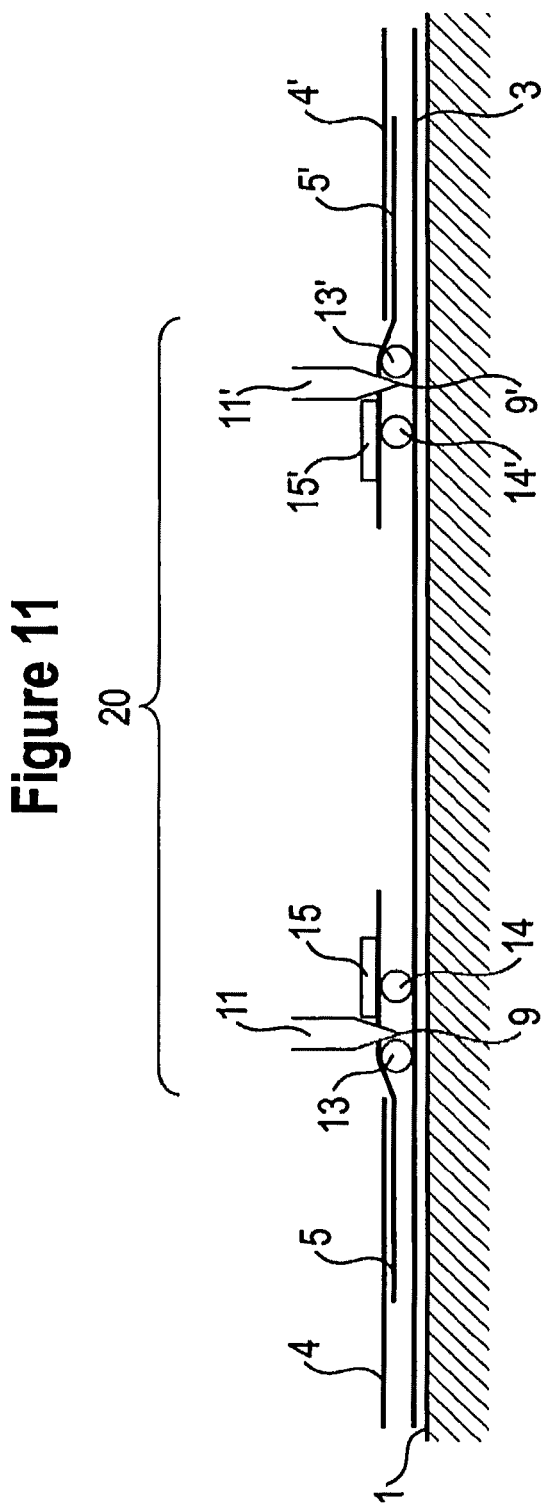
FIG. 11 shows a pair of cutting apparatus as shown in FIGS. 10 and 11 arranged side by side relative to the machine direction for respectively cutting adjacent rows of elastic waves.

Referring back to FIGS. 4 and 5 and the application of the cutting means and method of FIGS. 10 and 11 thereto, the opposed protruding portions of the elastic threads 500, 502 are trimmed away respectively using a first trimming apparatus as shown in FIG. 10 and a second trimming apparatus as shown in FIG. 10 arranged as shown in FIG. 11. Thus, the first trimming apparatus of FIG. 10 will operate on the elastic portions 500 protruding from the laminate of first and second webs 300, 200 and the second trimming apparatus of FIG. 10 will be arranged adjacent the first trimming apparatus to operate on the elastic threads 502 protruding from the laminate of the first and third webs 300, 700 according to the arrangement shown in FIG. 11. Opposed first and second grasping belts 14, 15 will respectively grasp the protruding portions of the first elastic threads 500 in an elevated position above the first web 300 and the third and fourth grasping belts 14', 15' will grasp the protruding portions of the second elastic threads 502 in an elevated position from the first web 300. Opposed first and second elevation elements 13, 13' which are held in a fixed manner so that the support surface 1 or the outer periphery of the rotating drum 620 and the first web 300 moves relative to them, are positioned adjacent the central edge 203, 703 of the second and third webs 200, 700 and serve to respectively elevate the protruding portions of the first and second elastic threads 500, 502.

The belts 14, 15, 14', 15' move in conjunction with the outer peripheral support surface of the rotating drum, whereby grasping belts 14, 15, 14', 15' sit atop the first web such that they all move together with no relative movement in the machine direction therebetween. The first elevation elements 13, 13' are held fixed relative to the moving support surface of the rotating drum 620 and thus the first web 300 relatively moves underneath it, preferably so that the first elevation elements are marginally spaced above the first web 300. The elastic threads 500, 502 respectively bridge the elevation elements 13, 13' and the elevation elements 14, 14' of the grasping means 14, 15, 14', 15' and the grasping means 14, 15, 14', 15' holds the bridge of elastic threads 500, 502 in a taut condition. The reverse rotating blades 9, 9' respectively protrude through the thickness of the bridge of elastic threads 500, 502 into the free space defined in the cavity formed by the elevation elements 13, 14 and 13', 14' and the support surface 1 to trim the threads 500, 502 from webs 300, 200, 700 as they move in the machine direction into engagement with the blades 9, 9'.

A further modification to the cutting apparatus of FIG. 4 (apart from the arrangement of the elevating and trimming means described above with respect to FIGS. 9, 10 and 11) is shown in FIG. 12. Referring to FIG. 4, it can be seen that the first and third grasping belts 402, 404 will be positioned on the rotating drum side of the first web 300 and so the first and second belts 401, 402 grasp the first web and the first elastic threads 500 therebetween and the third and fourth belts 403, 404 grasp the first web and the second elastic threads 502 therebetween. A preferred implementation of the present disclosure, however, requires the first and third belts to raise the elastic threads 500, 502 from the first web 300. In order to do so, in a preferred embodiment, the first and third belts 14, 14' are fed to the support surface 1 so to be positioned on the other side of the first web 300 to the support surface 1 of the rotating drum 620 so as to be positioned above the first web 300, between the first web 300 and the elastic threads 500, 502, as illustrated in FIG. 12.

In FIG. 12, there is shown first and second rollers 1000, 1002 forming a nip 400 therebetween at which nip 400 the first, second and third webs 300, 200, 700 and the elastic threads 500, 502 are laminated together. As can be seen in FIG. 12, the feed of the first and third belts 14, 14' is arranged to pass between the first and second rollers 1000, 1002 so that the elastic threads 500, 502 and the second and third webs 200, 700 are on one side of the first and third belts 14, 14' and the first web is positioned on the opposite side. The elastic threads 500, 502 are then respectively grasped between the first and second belts 14, 15 and the third and fourth belts 14', 15' as they pass through the lamination nip 400 between the first and second roller 1000, 1002 and the nip between the second roller 1002 and the drum 620. The belts 14, 15, 14', 15' are thus able to raise the elastic threads 500, 502 relative to the first web 300 and relative to the support surface 1 of the drum 620 for trimming away from the first web 300 when the elastic threads 500, 502 are in the elevated position. This can be compared to the arrangement of the prior art of FIG. 4, which is not able to independently move the threads 500, 502 from the first web 300 since the first and second belts 401, 402, 403, 404 nip the elastic threads 500, 502 to the first web 300 by sandwiching these elements between opposed belts 401, 402, 403, 404. Preferably, the second roller 1002 is provided with circumferential slots (not shown) to respectively accommodate the first and second belts 14, 15 and the second and third belts 14', 15' in the nip with the first roller 1000 without protruding into the plane of the first web 300 and the support surface of the first roller 1000.

The above detailed description provides exemplary implementations of the general concepts of the present disclosure, which concepts are defined in the following claims.

The invention claimed is:

1. A method of trimming material from a web in a method of manufacturing an absorbent article, the trimming method comprising:
    feeding the web and holding it against a support surface;
        holding material to be trimmed in an elevated position wherein an elevation element is used to contact and hold the material elevated above the support surface such that a knife blade severs the elevated material as it is positioned over the elevation element;
    trimming the elevated material from the web with a knife blade that is spaced from the support surface.

2. The method of claim 1, where the material to be trimmed is part of an elastic layer attached to the web.

3. The method of claim 1, wherein the knife blade protrudes beyond the elevated material in the thickness direction of the elevated material toward the support surface yet is spaced from the support surface.

4. The method of claim 1, wherein the elevated material is held taut against the elevation element so that the knife blade severs the taut elevated material.

5. The method of claim 1, wherein the web is fed in the machine direction by corresponding movement of the support surface in the machine direction.

6. The method of claim 1, wherein the support surface moves in the machine direction relative to the elevation element.

7. The method of claim 1, wherein the material is so grasped by a grasping means or clamped by a clamping means that moves in conjunction with the support surface as to hold the material taut during trimming with the knife blade.

8. The method of claim 1, wherein the material is so grasped by a grasping means or clamped by a clamping means that moves in conjunction with the support surface as to hold the material taut during trimming with the knife blade in a taut condition against the elevation element.

9. The method of claim 1, wherein the elevated material spans first and second elevation elements for elevating the material from the support surface in a taut manner, whereby the knife blade is positioned between the elevation elements to trim the elevated material.

10. The method of claim 1, wherein an elevation element for carrying out the elevating of the material from the support surface is arranged so that the web is able to travel underneath it as the material travels above it, thereby elevating the material from the web so that it can be trimmed by the knife blade.

11. The method of claim 1, wherein the web travels positioned underneath an elevation element for elevating the material from the support surface and a grasping means, whereby the grasping means and the elevation element holds the material in an elevated position relative to the support surface and the grasping means holds the material taut against the elevation element and the knife blade is positioned between the elevation element and the grasping means in the cross-machine direction so as to cut through the material yet remain spaced from the support surface and the underlying web, whereby the grasping means and the support surface move correspondingly in the machine direction relative to the knife blade so that the elevated material is trimmed from the web as the material and the web move in the machine direction and the web thus comes into contact with the knife blade.

12. The method of claim 1, wherein the knife blade is rotated in a reverse rotational direction relative to the direction of movement of the elevated material that moves in the machine direction in conjunction with the web.

13. The apparatus of claim 1, comprising a rotary cutter having the knife blade provided by a circumferential surface thereof, wherein the rotary cutter is set to rotate in a reverse direction to the movement of the web and the elevated material, which move in conjunction in the machine direction.

14. A method of manufacturing an elasticised web in a method of manufacturing an absorbent article, the elasticised web having discrete elastic portions separated from one another in a machine or longitudinal direction of the elasticised web, the method of manufacturing the elasticised web comprising:
  feeding a first web supported on a support surface in a machine direction;
  partly attaching an elastic layer to the first web so as to define an undulating path along the first web in the machine direction;
  grasping an unattached portion of the elastic layer;
  holding the unattached portion elevated from the support surface; and
  trimming the unattached portion of the elastic layer while it is grasped, elevated and moving in the machine direction with the first web using a knife blade that protrudes through the thickness of the elevated portion of the layer toward the support surface yet spaced from the support surface to thereby cut the elastic layer into discrete portions separated from one another in the machine direction.

15. The method of claim 14, wherein a second web is laminated to the first web so as to sandwich the attached portions of the elastic layer between them and so that the unattached portions protrude in the cross machine direction from the laminate to be so grasped, elevated and trimmed.

16. The method of claim 14, wherein the elastic layer is in the form of a plurality of adjacent elastic threads for forming leg elastics of the absorbent article.

17. A method comprising the method of claim 14, wherein the elasticised web is used to form front waist regions, rear waist regions or both of absorbent articles such that the discrete elastic portions form leg elastics for the absorbent articles, to thereby manufacture absorbent articles.

18. An apparatus for trimming material from a web, the apparatus comprising:
  a moving support surface for feeding the web held thereagainst in a machine direction;
  an elevation element for contacting and elevating material attached to or part of the web from the support surface; and
  a knife blade positioned to protrude through the thickness of the elevated material as it is held in the elevated position by the elevation element and yet be spaced from the support surface to thereby trim material from the web.

19. The apparatus of claim 18, comprising a grasping means for holding the material to be cut in a fixed position relative to the moving web and for holding the material taut against the elevation element in the elevated position, whereby the knife blade is positioned between the grasping means and the elevation element to cut through the taut, elevated material.

20. The apparatus of claim 18, further comprising an elastic layer applicator that partly attaches an elastic layer to the first web such that the elastic layer extends in the machine direction and undulates in the cross machine direction to follow an undulating path and such that a first cross machine directional part of the undulating path is attached to the web and a second cross machine directional part of the undulating path is unattached to the web, whereby the elevation element is positioned to elevate the unattached part of the elastic layer and the knife blade is positioned to trim the elevated, unattached part of the elastic layer from the web, thereby forming discrete elastic portions separated from one another in the machine direction.

21. The apparatus of claim 20, comprising a second web feeding mechanism arranged to bring said web, which is a first web, and said second web together and a laminator to form a laminate sandwiching the elastic layer between the first and second webs, whereby the unattached part of the elastic layer protrudes in the cross machine direction from the laminate.

22. The apparatus of claim 21, comprising a converter taking the laminate of the first and second webs having the attached part of the elastic layer sandwiched therebetween and the unattached part trimmed away by the knife blade and converting it into at least front waist regions or rear waist regions of absorbent articles such that the space in the machine direction between the discrete elastic portions is made into absorbent core receiving crotch regions of the at least front or rear waist regions of absorbent articles and the elastic portions on either side of the absorbent cores form leg elastics for respective leg openings of the at least front or rear waist regions of the absorbent articles.

23. The apparatus of claim 18, wherein the support surface is formed by the outer surface of a rotating drum.

24. The apparatus of claim 18, wherein the elevation element is arranged relative to the support surface so that the web is able to be positioned underneath the elevation element and remain held against the support surface as the material to be trimmed away is positioned over the elevation element so as to be held in an elevated position relative to the web and the support surface for cutting through its thickness with the knife blade that is positioned to protrude through the thickness of the elevated material yet remain spaced from the web and the support surface.

25. The apparatus of claim 24, wherein the elevation element is fixed in the machine direction relative to the support surface so that the material to be trimmed away moves in the machine direction relative to the elevation element.

* * * * *